US011250580B2

(12) United States Patent
Meyer et al.

(10) Patent No.: US 11,250,580 B2
(45) Date of Patent: Feb. 15, 2022

(54) METHOD, SYSTEM AND COMPUTER READABLE STORAGE MEDIA FOR REGISTERING INTRAORAL MEASUREMENTS

(71) Applicant: DENTSPLY SIRONA INC., York, PA (US)

(72) Inventors: Marcel Meyer, Bensheim (DE); Sascha Schneider, Mühltal (DE); Anders Adamson, Darmstadt (DE); Ruwen Schnabel, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 64 days.

(21) Appl. No.: 16/580,084

(22) Filed: Sep. 24, 2019

(65) Prior Publication Data

US 2021/0090272 A1    Mar. 25, 2021

(51) Int. Cl.
| | |
|---|---|
| *G06K 9/00* | (2006.01) |
| *G06T 7/33* | (2017.01) |
| *G06N 20/00* | (2019.01) |
| *G06N 3/08* | (2006.01) |
| *G06T 7/00* | (2017.01) |
| *G06T 17/20* | (2006.01) |

(52) U.S. Cl.
CPC ............... *G06T 7/344* (2017.01); *G06N 3/08* (2013.01); *G06N 20/00* (2019.01); *G06T 7/0012* (2013.01); *G06T 17/205* (2013.01); *G06T 2207/10024* (2013.01); *G06T 2207/10028* (2013.01); *G06T 2207/20081* (2013.01); *G06T 2207/20084* (2013.01); *G06T 2207/30036* (2013.01); *G06T 2210/41* (2013.01)

(58) Field of Classification Search
CPC .................................................... A61B 5/0088
See application file for complete search history.

(56) References Cited

U.S. PATENT DOCUMENTS

| | | | |
|---|---|---|---|
| 7,698,068 | B2 | 4/2010 | Babayoff |
| 9,436,868 | B2 | 9/2016 | Dillon |
| 9,456,754 | B2 | 10/2016 | Kocherscheidt |
| 9,788,917 | B2 | 10/2017 | Mah |

(Continued)

FOREIGN PATENT DOCUMENTS

| | | |
|---|---|---|
| DE | 102011080180 A1 | 2/2013 |
| EP | 2428913 A2 | 3/2012 |

(Continued)

OTHER PUBLICATIONS

International Search Report; PCT/US2020/051942; dated Nov. 24, 2020 (completed); Dec. 2, 2020 (mailed).

(Continued)

*Primary Examiner* — Hadi Akhavannik
(74) *Attorney, Agent, or Firm* — Dentsply Sirona Inc.

(57) ABSTRACT

A method, system and computer readable storage media for segmenting individual intra-oral measurements and registering said individual intraoral measurements to eliminate or reduce registration errors. An operator may use a dental camera to scan teeth and a trained deep neural network may automatically detect portions of the input images that can cause registration errors and reduce or eliminate the effect of these sources of registration errors.

12 Claims, 11 Drawing Sheets

(i) Single Scan (ii) Single Scan (iii) Robust Registration (iv) Erroneous Registration

(56) References Cited

U.S. PATENT DOCUMENTS

| | | | | |
|---|---|---|---|---|
| 2002/0028418 | A1* | 3/2002 | Farag | A61C 9/0053 |
| | | | | 433/29 |
| 2010/0061601 | A1* | 3/2010 | Abramoff | G06T 7/33 |
| | | | | 382/117 |
| 2013/0343641 | A1* | 12/2013 | Mnih | G06K 9/6269 |
| | | | | 382/156 |
| 2014/0114742 | A1* | 4/2014 | Lamontagne | G06Q 30/0242 |
| | | | | 705/14.41 |
| 2014/0177931 | A1 | 6/2014 | Kocherscheidt | |
| 2017/0281110 | A1* | 10/2017 | Mandelkern | G06T 7/181 |
| 2017/0337682 | A1* | 11/2017 | Liao | G06T 7/30 |
| 2018/0028294 | A1 | 2/2018 | Azernikov | |
| 2018/0161986 | A1* | 6/2018 | Kee | G06T 7/75 |
| 2019/0026893 | A1 | 1/2019 | Salah | |
| 2019/0050999 | A1* | 2/2019 | Piat | G06T 15/08 |
| 2019/0333199 | A1* | 10/2019 | Ozcan | G06N 3/088 |
| 2019/0369030 | A1* | 12/2019 | Wu | G06T 7/33 |

FOREIGN PATENT DOCUMENTS

| | | |
|---|---|---|
| WO | 2013017617 A1 | 2/2013 |
| WO | 2018158411 A1 | 9/2018 |
| WO | 2018219800 A1 | 12/2018 |
| WO | 2019158442 A1 | 8/2019 |

OTHER PUBLICATIONS

Written Opinion of the International Searching Authority; PCT/US2020/051942; dated Nov. 24, 2020 (completed); Dec. 2, 2020 (mailed).
"Recurrent Convolutional Neural Networks; A Better Model of Biological Object Recognition"; Courtney J. Spoerer et al.; Front. Psychol., Sep. 12, 2017.
Fully Convolutional Networks for Semantic Segmentation; Jonathan Long et al.; Mar. 8, 2015.

* cited by examiner

METHOD, SYSTEM AND COMPUTER READABLE STORAGE MEDIA FOR REGISTERING INTRAORAL MEASUREMENTS

FIELD OF THE INVENTION

The present application relates generally to a method, a system and computer readable storage media for registering in intraoral measurements and, more particularly, to a method, system and computer readable storage media for utilizing deep learning methods to semantically register intraoral measurements.

BACKGROUND OF THE INVENTION

Dental practitioners may be trained to generate satisfactory acquisition results during scanning by using appropriate scanning techniques such as keeping soft tissue outside of a dental camera's field of view. Soft tissue may deform during scanning, leading to multiple shapes of the same area and thereby introducing errors and/or interruptions during registration.

Currently, feature based techniques such as Fast Point Feature Histograms (FPFH) may be used to compute transformations through which scans/three-dimensional (3D) measurements may be registered without prior knowledge of the relative orientation of the scans. However for these techniques to work, it may be required to avoid the scanning/3D measurement of regions that are deformable.

U.S. Pat. No. 9,456,754B2 discloses a method of recording multiple three-dimensional images of a dental object, wherein each of the three-dimensional images may include 3D measured data and color data of a measured surface of the object, wherein the individual images are combined into an overall image using a computer-assisted recording algorithm. It is incorporated herein by reference for all purposes as if fully set forth herein.

U.S. Pat. No. 7,698,068B2 discloses a method of providing data useful in procedures associated with the oral cavity by providing at least one numerical entity representative of the three-dimensional surface geometry and color of at least part of the intra-oral cavity; and manipulating the entity to provide desired data therefrom. Typically, the numerical entity includes surface geometry and color data associated with said part of the intra-oral cavity, and the color data includes actual or perceived visual characteristics including hue, chroma, value, translucency, and reflectance.

WO2018219800A1 discloses a method and apparatus for generating and displaying a 3D representation of a portion an intraoral scene including determining 3D point cloud data representing a part of the intraoral scene in a point cloud coordinate space. A color image of the same part of the intraoral scene is acquired in camera coordinate space. The color image elements that are within a region of the image representing a surface of said intraoral scene are labelled.

U.S. Pat. No. 9,436,868B2 discloses methods that enable rapid automated object classification of measured three-dimensional (3D) object scenes. An object scene is illuminated with a light pattern and a sequence of images of the object scene illuminated by the pattern at different spatial phases is acquired.

U.S. Pat. No. 9,788,917B2 discloses a method for employing artificial intelligence in automated orthodontic diagnosis and treatment planning. The method may include providing an intraoral imager configured to be operated by a patient; receiving patient data regarding the orthodontic condition; accessing a database that comprises or has access to information derived from orthodontic treatments; generating an electronic model of the orthodontic condition; and instructing at least one computer program to analyze the patient data and identify at least one diagnosis and treatment regimen of the orthodontic condition based on the information derived from orthodontic treatments.

U.S. Patent Application Publication No. 20190026893A1 discloses a method for assessing the shape of an orthodontic aligner wherein an analysis image is submitted to a deep learning device, in order to determine a value of a tooth attribute relating to a tooth represented on the analysis image, and/or at least one value of an image attribute relating to the analysis image.

PCT Application PCT/EP2018/055145 discloses a method for constructing a restoration in which a dental situation is measured by means of a dental camera and a three-dimensional (3D) model of the dental situation is generated. A computer-assisted detection algorithm may then be applied to the 3D model of the dental situation and a type of restoration, a tooth number or a position of the restoration are automatically determined.

U.S. Application Publication No. 20180028294A1 discloses a method for Dental CAD Automation using deep learning. The method may include receiving a patient's scan data representing at least one portion of the patient's dentition data set; and identifying, using a trained deep neural network, one or more dental features in the patient's scan. Herein, design automation may be carried out after complete scans have been generated. However this method does not improve the actual scanning process.

WO2018158411A1 discloses a method for constructing a restoration, in which a dental situation is measured by means of a dental camera and a 3D model of the dental situation is generated. In this case, a computer-assisted detection algorithm is applied to the 3D model of the dental situation, wherein a type of restoration and/or at least a tooth number and/or a position of the restoration to be inserted are automatically determined.

SUMMARY OF THE INVENTION

Existing limitations associated with the foregoing, as well as other limitations, can be overcome by a method, system and computer readable storage media for utilizing deep learning methods to semantically register intraoral measurements.

In an aspect herein, the present invention may provide computer implemented method for three-dimensional (3D) registration, the method comprising: receiving, by one or more computing devices, individual images of a patient's dentition; automatically identifying sources of registration errors in the individual images using one or more output labels such as output probability values of a trained deep neural network, wherein the output labels/probability values are obtained by segmenting the individual images into regions corresponding to one or more object categories; wherein the individual images are depth and/or corresponding color images; the method further comprising registering the individual images together based the one or more output labels such as probability values to form a registered 3D image having no registration errors or substantially no registration errors.

In another aspect herein, the computer implemented method may further comprise one or more combinations of the following steps: (i) wherein the registration is achieved by: generating a point cloud from the depth images by projecting pixels of the depth images into space; assigning color values and label/probability values to each point in the point cloud using the corresponding color images and the output label/probability values of the trained deep neural network respectively; and based on the assigned label/probability values, discarding or partially including points in the point cloud using predetermined weights, such that the contributions of the discarded or partially included points to registration is eliminated or reduced, (ii) wherein the individual images are individual three dimensional optical images, (iii) wherein the individual images are received as a temporal sequence of images, (iv) wherein the individual images are received as a pair of color and depth images, (v) wherein the one or more object categories include hard gingiva, soft tissue gingiva, tooth and tooth-like objects, (vi) wherein an indication of a relevance of an identified source of registration error are based on its surrounding geometry, (vii) wherein the deep neural network is a network chosen from the group consisting of a Convolutional Neural Network (CNN), a Fully Convolutional Neural Network (FCN), a Recurrent Neural Network (RNN) and a Recurrent Convolutional Neural Network (Recurrent-CNN), (vii) further comprising: training the deep neural network using the one or more computing devices and a plurality of individual training images, to map one or more tissues in at least one portion of each training image to one or more label/probability values, wherein the training is done on a pixel level by classifying the individual training images, pixels of the individual training images, or super pixels of the individual training images into one or more classes corresponding to semantic data types and/or error data types, (viii) wherein the training images include 3D meshes and registered pairs of depth and color images, (ix) wherein the 3D meshes are labelled and the labels are transferred to the registered pairs of 3D and color images using a transformation function.

In yet another aspect of the present invention, a non-transitory computer-readable storage medium storing a program may be provided, which, when executed by a computer system, causes the computer system to perform a procedure comprising: receiving, by one or more computing devices, individual images of a patient's dentition; automatically identifying sources of registration errors in the individual images using one or more output probability values of a trained deep neural network, wherein the output probability values are obtained by segmenting the individual images into regions corresponding to one or more object categories; wherein the individual images are depth and/or corresponding color images; the method further comprising registering the individual images together based the one or more output probability values to form a registered 3D image having no registration errors or substantially no registration errors.

Further, a system for three-dimensional (3D) registration, may be provided, the system comprising a processor configured to: receive, by one or more computing devices, individual images of a patient's dentition; automatically identify sources of registration errors in the individual images using one or more output probability values of a trained deep neural network, wherein the output probability values are obtained by segmenting the individual images into regions corresponding to one or more object categories; wherein the individual images are depth and/or corresponding color images; wherein the processor is configured to register the individual images together based the one or more output probability values to form a registered 3D image having no registration errors or substantially no registration errors.

In a further aspect of the present invention, the system a deep neural network which is chosen from the group consisting of a Convolutional Neural Network (CNN), a Fully Convolutional Neural Network (FCN), a Recurrent Neural Network (RNN) and a Recurrent Convolutional Neural Networks (Recurrent-CNN).

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Figure 1:
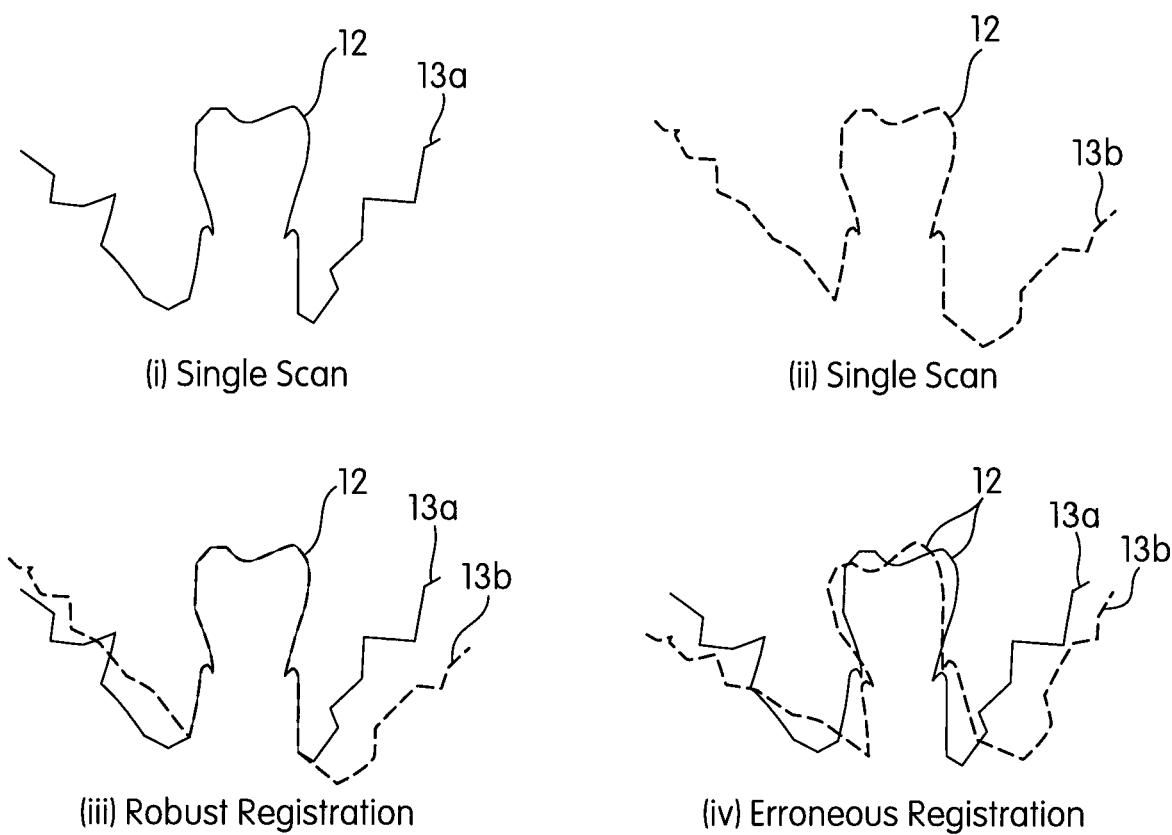
FIG. 1 is a sketch of a cross section of an oral cavity illustrating different surrounding geometry due to deformation of soft tissue.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method, system and computer readable storage media may be provided for utilizing deep learning methods to semantically segment individual intra-oral measurements and register said individual intraoral measurements.

System for Registering Intraoral Measurements

The accurate 3D measurement of a patient's oral cavity may be hindered by erroneous registration. In intraoral measurement of jaws cameras are employed, that produce single scans, capturing only a subset of the entire jaw, which may be registered together to form a complete model. The camera may be hand-held and the exact positions from where the single scans are obtained is generally unknown. Based on the information from these single scans (such as 3D-data, color data) transformations are determined in order to bring the single scans into a common reference frame (a common 3D coordinate system). However parts of the oral cavity that get deformed/change shape while the camera is acquiring many single scans at high frequency may distort registration since most registration processes operate under the assumption of rigidity. Thus, only rigid parts are be considered for registration.

Since the scans are taken at different points in time, the geometry of certain tissues (particularly soft tissues of the oral cavity) may change during the time period between the different scans due to deformation of soft tissue or presence of moving foreign objects. This may impede registrations that rely on matching 3D-data (see FIG. 1, showing typical errors, produced by, e.g. techniques based on a minimizing the sum of squares error).

Figure 2A:
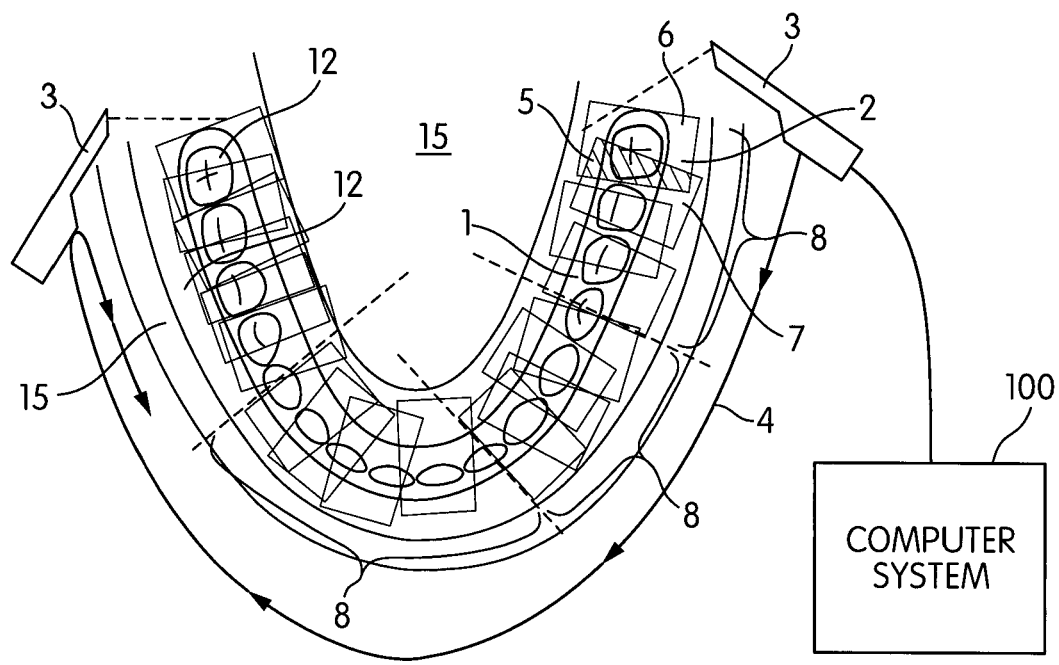
FIG. 2A is a sketch of a top view of an oral cavity illustrating the scanning/recording of individual images of a patient's dentition.

An improvement of these techniques may be achieved, by only considering rigid parts for registration and by discarding irrelevant (i.e. non-rigid) parts or weighing their contribution to the registration less, i.e. when rigid parts/hard tissue 12 such as a tooth are considered for registration, the registration is robust (iii) and the surrounding geometries 13a, 13b of the rigid parts/hard tissue 14 are in alignment, and vice versa (iv) as shown in FIG. 1. The term "rigid" may thus be used hereinafter to describe an anatomy or a part of an anatomy that may be unlikely to be deformed during the period of time in which a scan procedure is being performed. Gums close to the tooth may be deformed if a high enough force is applied to it, but during scanning with an intraoral scanner this may usually not be the case. So, considering it to be rigid would be a reasonable assumption. On the other hand the inner side of the cheek will likely be deformed from scan to scan and as such may be considered to be soft tissue/soft parts 15 (FIG. 2A).

The system described herein may preferably obtain images, such as individual three-dimensional optical images 2 (FIG. 2A), with each three-dimensional optical image 2 preferably comprising 3D measured data and color data of a measured surface of the teeth and preferably being recorded sequentially in an oral cavity through, a direct intraoral scan. This may occur, for example, in a dental office or clinic and may be performed by a dentist or dental technician. The images may also be obtained indirectly through a sequence of stored images.

Using the images, preferably obtained as a temporal sequence, a computer-implemented system may automatically identify areas in the images that may be considered for registration. This may be done in real-time. Of course the images may also be individual two-dimensional (2D) images, RGB Images, Range-Images (two-and-a-half-dimensional, 2.5D), 4-Channel Images (RGB-D), where depth and color may not be in perfect alignment, i.e. depth and color images may be acquired at different time periods.

Figure 4:
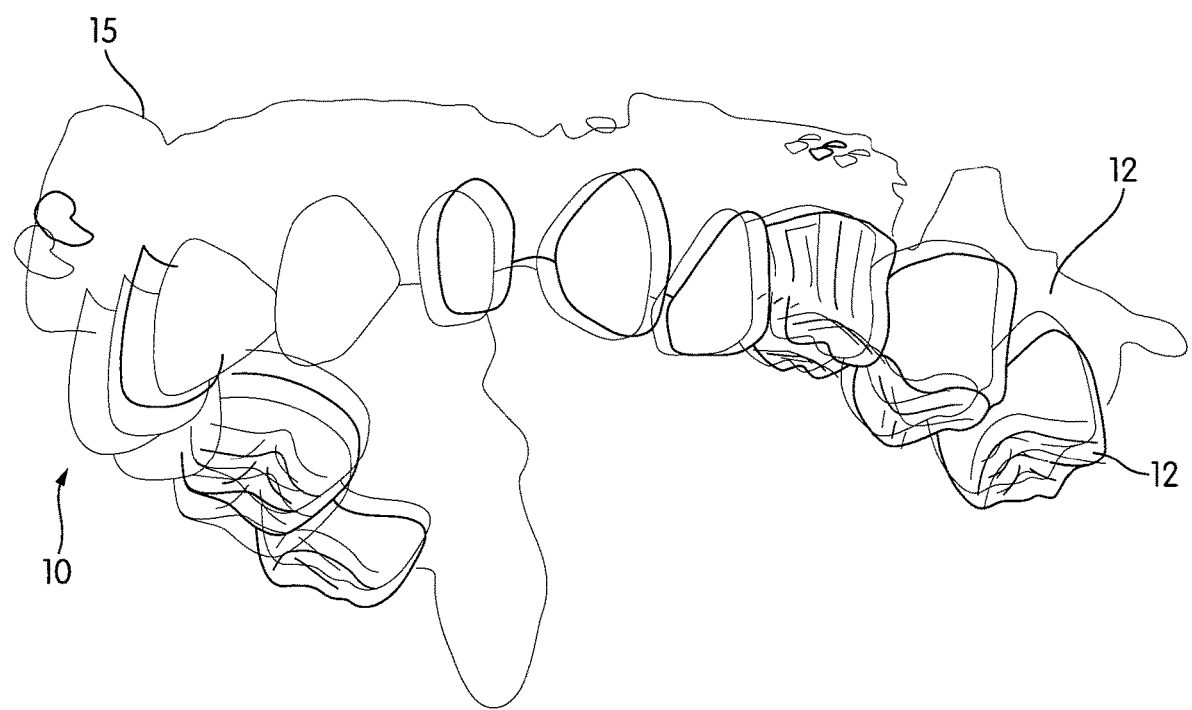
FIG. 4 is a perspective view of a global 3D image of a dentition formed from individual images having soft tissue.

In the scanning process, a plurality of individual images may be created and then a sequence 8 of at least two individual images or a plurality of sequences 8 may be combined to form an overall/global 3D image 10 (FIG. 4). More specifically, as shown in FIG. 2A, individual three-dimensional optical images 2, which are illustrated in the form of rectangles, may be obtained by means of a scanner/dental camera 3 which may be moved relative to the object 1 along a measurement path 4 during the measurement. In some embodiments, the measurement path may be any arbitrary path, i.e. the measurements may be taken from different directions. The dental camera 3 may be a handheld camera, for example, which measures the object 1 using a fringe projection method. Other methods of 3D measurement may be realized by persons of ordinary skill in the art. A first overlapping area 5 between a first image 6 and a second image 7, which is shown with a dashed line, is checked to determine if recording conditions are met by using a computer and if met, the three-dimensional optical images 2 may be combined/registered together to form a global 3D image 10.

The recording conditions may include an adequate size, an adequate waviness, an adequate roughness, and/or an adequate number and arrangement of characteristic geometries. However, it may be difficult to program a conventional computer to determine sources of registration errors and how to prevent them. Manually programming features used for registration or segmentation methods such that every possible scenario is covered may be tedious to do, especially considering the high frequency of measurement. This holds true especially if the context of the whole image is to be considered. Using machine learning approaches, in particular neural networks, and correct training data may solve the problem more effectively. A neural network on the other hand may learn to recognize the sources of registration errors and semantically segment data from single scans/single 3D measurements, and decide whether these areas of the oral cavity may be considered for registration. To this end labels for different objects/object categories of segmentations may be defined to include, but not limited to (i) Hard Tissue (such as teeth, crowns, bridges, hard gingiva near teeth, and other tooth-like objects), (ii) Soft Tissue (such as tongue, cheek, soft gingiva etc.) and (iii) Instruments/intraoral applied disposables (such as mirrors, scanbodies, cotton rolls, brackets etc.). Of course other definitions such as glaring 21 (FIG. 2B, caused by bright light) may be added as appropriate. The segmentations may be based on color, the color may be interpreted in a context aware manner i.e. an indication of a relevance of a potential source of registration error may be based on its surrounding geometries 13a, 13b. Moreover, the segmentations may be based on single pixels of color data or bigger regions of the individual three-dimensional optical images 2.

Since crowns, teeth or hard gingiva near teeth are rigid, registration errors may be eliminated or substantially reduced by registration algorithms that take correct segmentation into account. Furthermore by removing clutter introduced by accessories like cotton rolls, a cleaned up 3D model may be generated, said cleaned up 3D model containing just data relevant for dental treatment.

Figure 5:
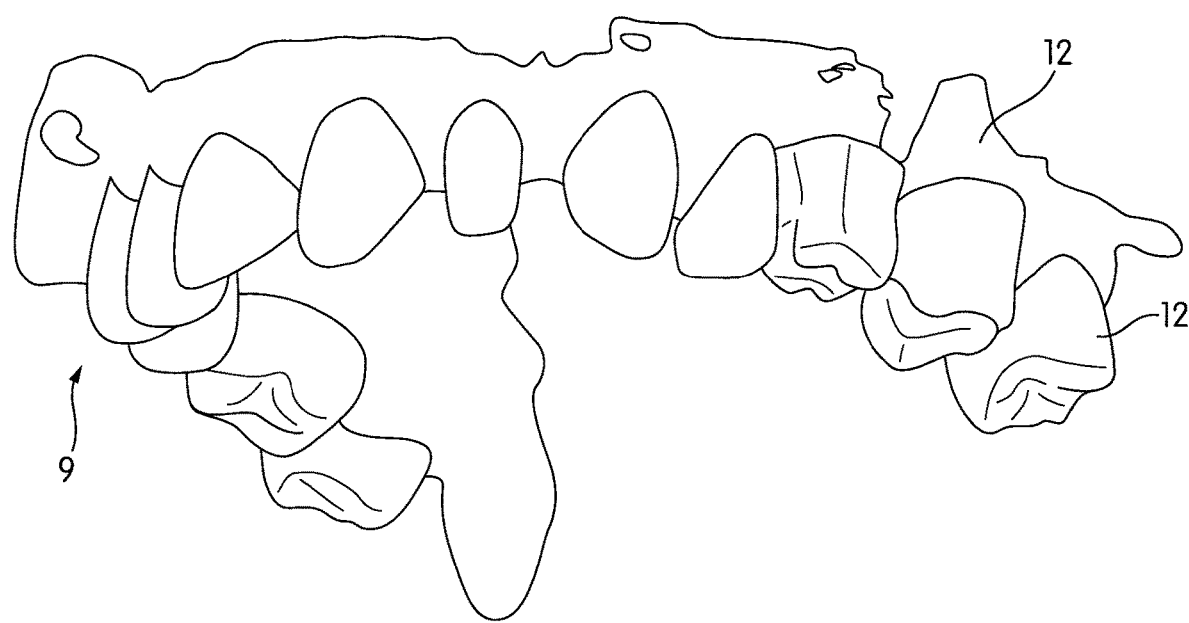
FIG. 5 is a perspective view of a corrected global 3D image of a dentition formed from individual images having soft tissue contributions removed or weighted less according to an embodiment of the present invention.

The system may therefore train neural networks such as deep neural networks, using a plurality of training data sets, to automatically recognize sources of registration errors in the three dimensional optical images 2, and prevent those sources from contributing to registration, preferably in real time. Therefore, erroneous registrations (FIG. 1, iv) propagated to the global 3D image 10 (FIG. 4) may be reduced or eliminated as shown in the corrected global 3D image 9 of FIG. 5 and/or the scan flow may be improved due to fewer/no interruptions caused by the erroneous registration.

The present system may also identify and label data semantically (in a context aware manner, i.e. the context may be important to select an appropriate corrective method. E.g. gums close to teeth may be considered as hard tissue 12, while gums that are away from teeth may be considered as soft tissue 15).

Figure 2B:
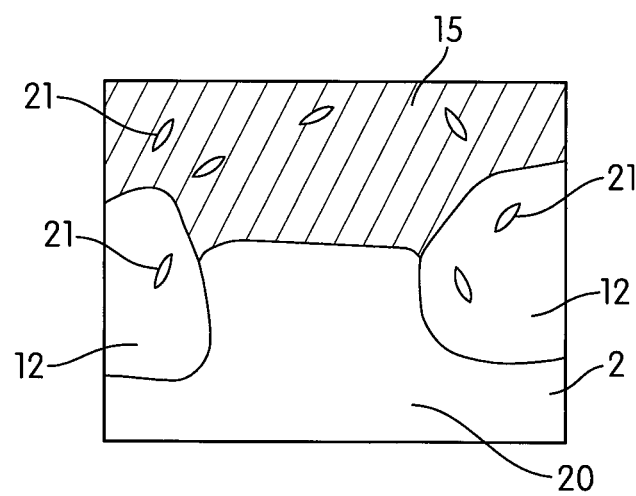
FIG. 2B is a sketch illustrating an example registration according to an embodiment of the present invention.

Moreover, the system may determine corrective measures and/or apply said determined corrective measures upon detecting the sources of registration errors. For example, when there is a high proportion of hard tissue 12 to soft tissue 15 in the individual three-dimensional optical image 2, it may be advantageous to weigh the hard tissue 12 much more than the soft tissue 15 because deformation or movement of the patient's cheek or lips may lead to deformation of the soft tissue and thus to a faulty recording as shown in FIG. 1 (iv). However, if the proportion of hard tissue 15 in the image is low, the soft tissue 15 may be weighted much more in order to improve the quality of the recording. As an example, FIG. 2B shows an image in which two middle teeth are missing so that a first area having hard tissue 12 amounts to about 10% of the total area of the individual three-dimensional optical image 2, and a second area having soft tissue 15 amounts to about 50% of the total area of the image. A remaining third area which cannot be assigned to any of the tissues amounts to about 40%; the percentage for the first area having hard tissue 12 falls below a predetermined threshold value of 30%. Consequently, the first area having hard tissue 12 is weighted with a first weighting factor and the second area having soft tissue is weighted with a second weighting factor, such that the second weighting factor increases with a decline in the first area. For example, the first weighting factor for the first area having hard tissue 12 may be 1.0, and the second variable weighting factor for the second area having soft tissue 15 may be 0.5 when the predetermined threshold value is exceeded, and up to 1.0 with a decline in the first area. The dependence of the second weighting factor on the first area may be defined according to any function such as an exponential function or a linear function and the hard tissue and soft tissue may be segmented using the neural network described herein.

Figure 3A:
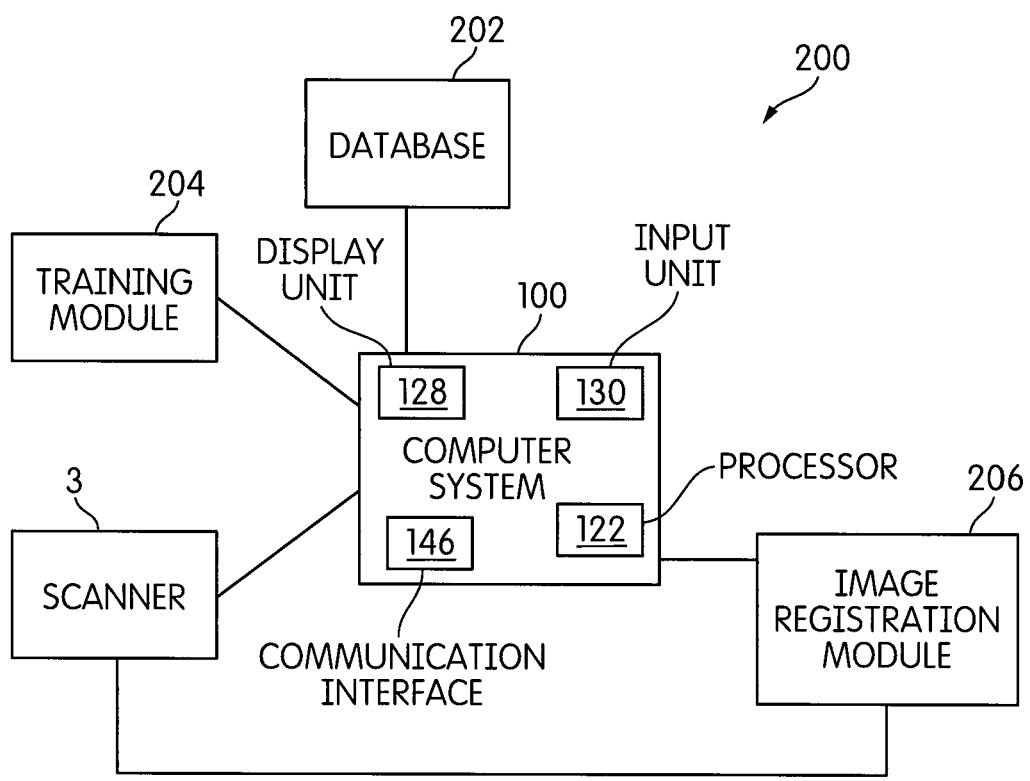
FIG. 3A is a high level block diagram of a system according to an embodiment of the present invention.

FIG. 3A shows a block diagram of a system 200 for recognizing dental information from individual three-dimensional optical images 2 of patients' dentitions according to one embodiment. System 200 may include a dental camera 3, a training module 204, an image registration module 206, a computer system 100 and a database 202. In another embodiment, the database 202, image registration module 206, and/or training module 204 may be part of the computer system 100 and/or may be able to directly and/or indirectly adjust parameters of the dental camera 3 based on a correction regimen. The computer system 100 may also include at least one computer processor 122, a user interface 126 and input unit 130. The computer processor may receive various requests and may load appropriate instructions, as stored on a storage device, into memory and then execute the loaded instructions. The computer system 100 may also include a communications interface 146 that enables software and data to be transferred between the computer system 100 and external devices.

The computer system 100 may receive registration requests from an external device such as the dental camera 3 or a user (not shown) and may load appropriate instructions for semantic registration. Preferably, the computer system may independently register images upon receiving individual three-dimensional optical images 2, without waiting for a request.

Figure 3B:
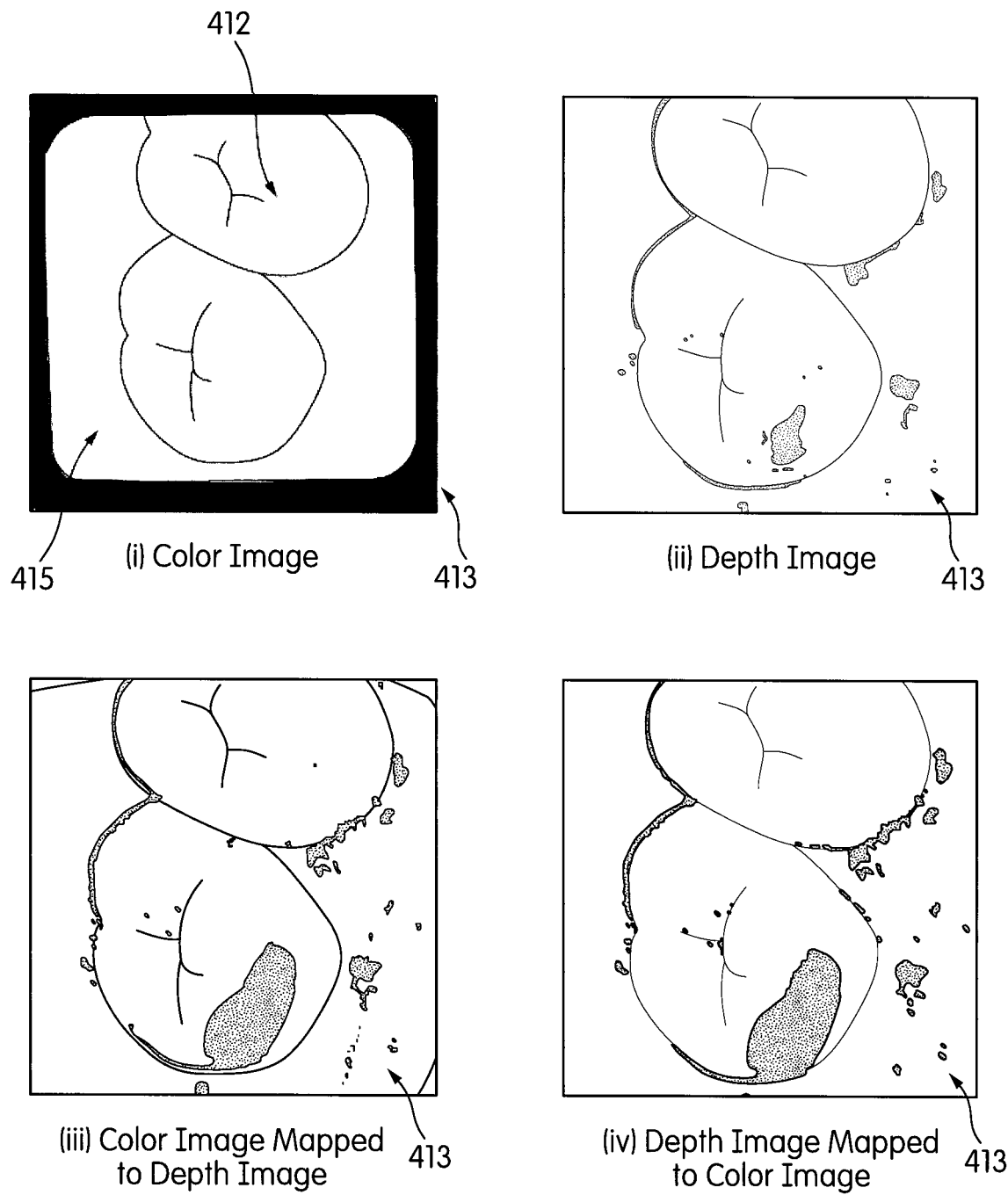
FIG. 3B shows example training images according to an embodiment of the present invention.

In one embodiment, the computer system 100 may use a plurality of training data sets from the database 202 (which may include, for example, a plurality of individual three-dimensional optical images 2) to train one or more deep neural networks, which may be a part of training module 204. FIG. 3B (I-IV) show examples images used for training including a color image, depth image, color image mapped to depth image and depth image mapped to color image, respectively. Mapping the images may be good for Convolutional Neural Networks (CNNs) since CNNs operate on local neighborhoods. So represent regions of the rgb and depth image may be represented with the same 2d-pixel coordinates. For example, mapping a depth image to a rgb image or vice versa means generating an image, such that the pixels with the same 2d-pixel coordinates in the rgb image and the generated image correspond to the same point in space. Usually this involves the application of pinhole camera models and a transformation accommodating for movement (determined by a registration algorithm). A step compensating for motion may be omitted and the net may be expected to be able to cope with the resulting offset which is expected to be small. In some embodiments, system 200 may include a neural network module (not shown) that contains various deep learning neural networks such as Convolutional Neural Networks (CNN), Fully Convolutional Neural Networks (FCN), Recurrent Neural Networks (RNN) and Recurrent Convolutional Neural Networks (Recurrent-CNN). An example fully Convolutional Neural Network is described in the publication by Jonathan Long et al, entitled "Fully Convolutional Networks for Semantic Segmentation", 8 Mar. 2015, which is hereby incorporated by reference in its entirety, as if set forth fully herein. Thus a fully convolutional neural network (efficient convolutional network architecture used for per pixel segmentation) may be trained to segment RGB(D)-Images or sequences of RGB(D)-images by employing a recurrent model. A recurrent model may be used as opposed to a simple feed forward network. Thus, the network may receive output of a layer as input for the next forward computation, such that its current activation can be considered a state depending on all previous input, thus enabling the processing of sequences. Moreover, an example Recurrent-CNN model is described in the publication by Courtney J. Spoerer et al, entitled "Recurrent Convolutional Neural Networks: A Better Model of Biological Object Recognition" Front. Psychol., 12 Sep. 2017, which is hereby incorporated by reference in its entirety, as if set forth fully herein.

The training data sets and/or inputs to the neural networks may be pre-processed. For example, in order to process color data in conjunction with 3D measurements a calibration (such as a determination of parameters of the camera model) may be applied to align color images with the 3D surface. Furthermore, standard data augmentation procedures such as synthetic rotations, scalings etc. may be applied to the training data sets and/or inputs.

The training module 204 may use training data sets with labels to supervise the learning process of the deep neural network. The labels may be used to weigh data points. The training module 204 may conversely use unlabeled training data sets to train generative deep neural networks.

In an example embodiment, to train a deep neural network to detect sources of registration errors, a plurality of real life individual three-dimensional optical image data sets, having tissue types and object categories described above may be used. In another example, to train the deep neural network to recognize semantic data (e.g., hard gingiva near teeth), another plurality of training data sets from real dental patients with one or more hard gingiva areas near one of more teeth and one or more soft gingiva areas away from one or more teeth are selected to form a group of training data sets. Database 202 may therefore contain different groups of training data sets, one group for each object category and/or for each semantic data type, for example.

In some embodiments, training module 204 may pre-train one or more deep neural networks using training data sets from database 204 such that the computer system 100 may readily use one or more pre-trained deep neural networks to detect the sources of registration errors. It may then send information about the detected sources and or the individual three-dimensional optical images 2, preferably automatically and in real time, to an image registration module 206 wherein the sources of registration errors will be taken into account prior to registration.

The database 204 may also store data related to the deep neural networks and the identified sources along with corresponding individual three-dimensional optical images 2. Moreover, the computer system 100 may have a display unit 126 and input unit 130 with which a user may perform functions such as submitting a request and receiving and reviewing identified sources of registration errors during training.

Figure 8:
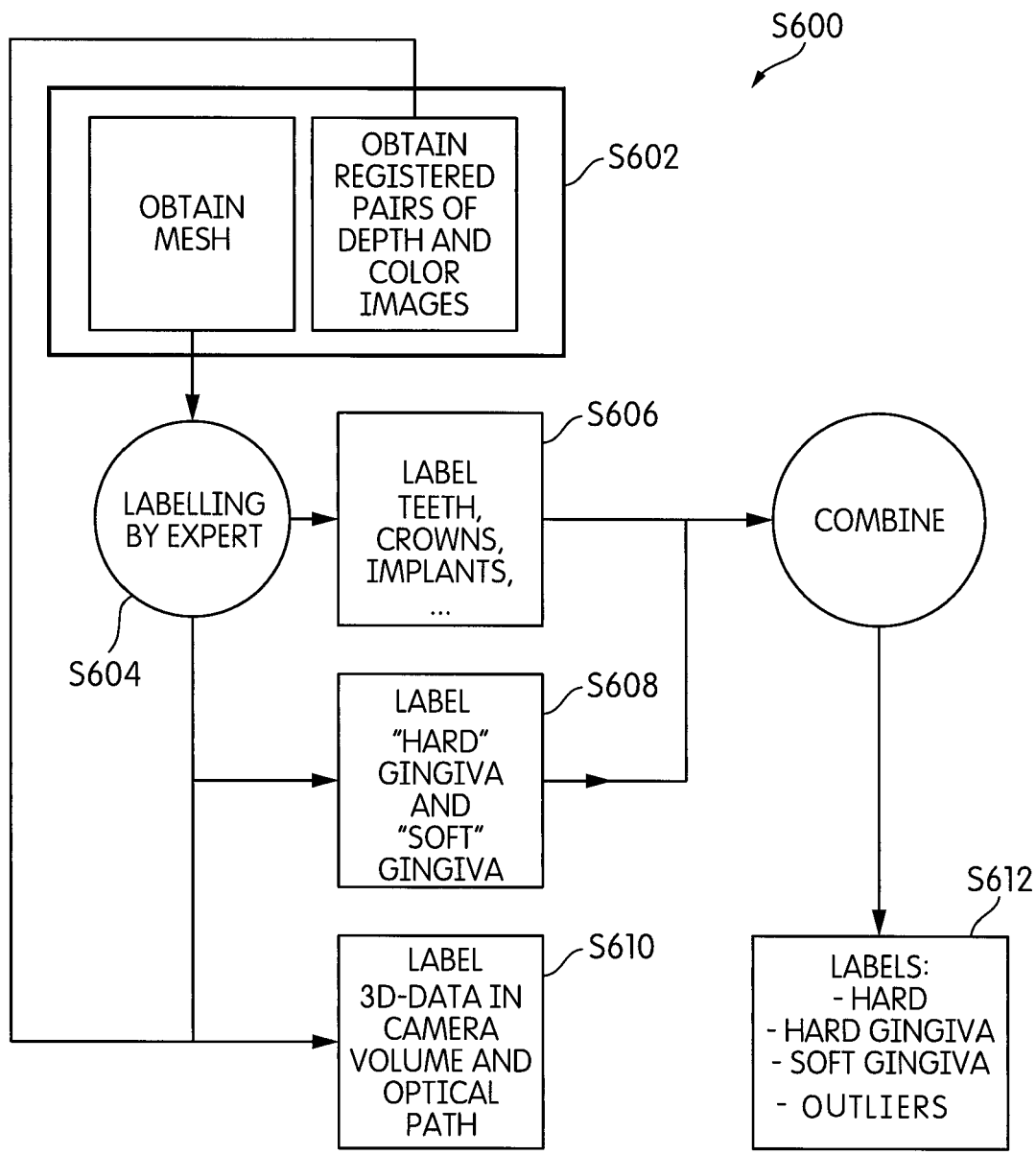
FIG. 8 is a block diagram illustrating a training method according to an embodiment of the present invention.

In an example embodiment of the training process, S600, as shown in FIG. 8, the labels may be generated by collecting images representing real cases in the field, Step S602. Contained in these cases may be meshes (such as a 3D triangle mesh) and single images (registered pairs of depth and color images). The meshes may be segmented by an expert who may cut out the teeth in the mesh. The cut out meshes may then be labelled, Step S604. They may be labelled as teeth, crowns, implants, or other tooth-like object (Step S606) or as hard gingiva and soft gingiva, (Step S608). Additionally, outliers such as 3D points in the optical path of the camera 3 that are not part of the oral cavity may be labelled, Step S610. The labeling of the meshes may be transferred to the pixels of the single images, thus reducing that amount of work done in the training process. All the final labels may be determined in Step S612 from combining information from Steps S606, S608 and S610 Step S612. Moreover knowing the transformations that aligned the single images together (since they are registered) these final labels may be transferred from the cut out meshes to the single images. In this way, many images may be labelled at once through the cutting/slicing of the mesh.

Other embodiments of the system 200 may include different and/or additional components. Moreover, the functions may be distributed among the components in a different manner than described herein.

Figure 6:
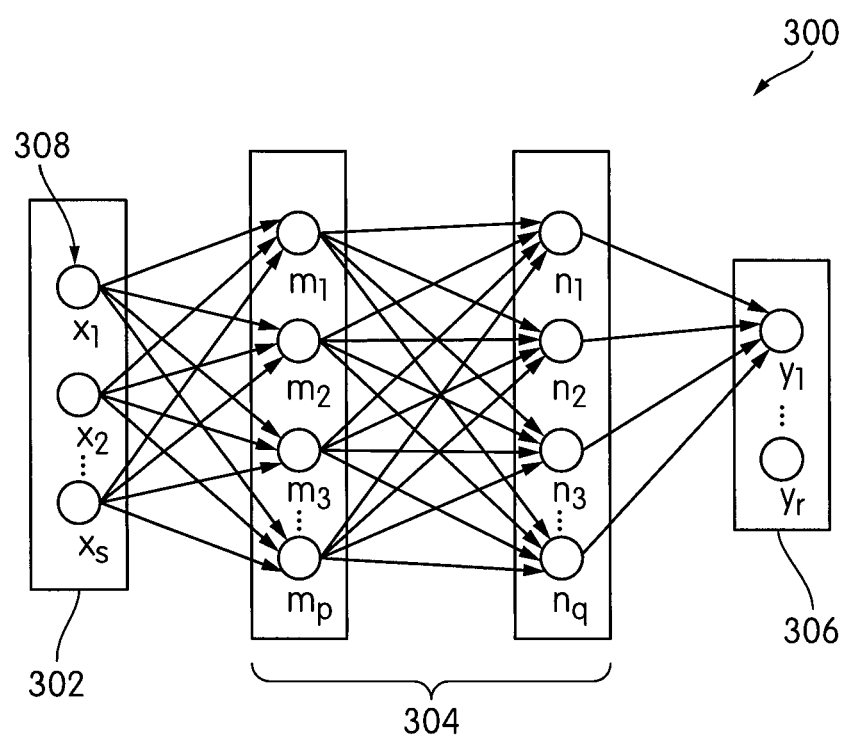
FIG. 6 is a high-level block diagram showing a structure of a deep neural network according to one embodiment.

FIG. 6 shows a block diagram illustrating a structure of a deep neural network 300 according to an embodiment of the present invention. It may have several layers including an input layer 302, one or more hidden layers 304 and an output layer 306. Each layer may consist of one or more nodes 308, indicated by small circles. Information may flow from the input layer 302 to the output layer 306, i.e. left to right direction, although in other embodiments, it may be from right to left, or both. For example, a recurrent network may take previously observed data into consideration when processing new data in a sequence 8 (e.g. current images may be segmented taking into consideration previous images), whereas a non-recurrent network may process new data in isolation.

A node 308 may have an input and an output and the nodes of the input layer 308 may be passive, meaning they may not modify the data. For example, the nodes 308 of the input layer 302 may each receive a single value (e.g. a pixel value) on their input and duplicate the value to their multiple outputs. Conversely, the nodes of the hidden layers 304 and output layer 306 may be active, therefore being able to modify the data. In an example structure, each value from the input layer 302 may be duplicated and sent to all of the hidden nodes. The values entering the hidden nodes may be multiplied by weights, which may be a set of predetermined numbers associated with each of the hidden nodes. The weighted inputs may then be summed to produce a single number.

In an embodiment according to the present invention, the deep neural network 300 may use pixels of the individual three-dimensional optical images 2 as input when detecting the object categories. The individual three-dimensional optical images 2 may be color images and or depth images. Herein, the number of nodes in the input layer 302 may be equal to the number of pixels in an individual three-dimensional optical image 2.

In an example embodiment, one neural network may be used for all object categories and in another embodiment, different networks may be used for different object categories. In another example, the deep neural network 300 may classify/label the individual three-dimensional optical images 2 instead of individual pixels when detecting object categories such as those caused by ambient light. In a further embodiment, the images may be subsampled inputs, such as every $4^{th}$ pixel.

In yet another embodiment, the deep neural network 300 may have as inputs a plurality of data acquired by the dental camera 3 such as color-images, depth measurements, accelerations as well as device parameters such as exposure times, aperture etc. The deep neural network may output labels which may be, for example, a probability vector that includes one or more probability values of each pixel input belonging to certain object categories. For example, the output may contain a probability vector containing probability values wherein the highest probability values may define locations of the hard tissues 12. The deep neural network may also output a map of label values without any probabilities. A deep neural network can be created for each classification though that may not be necessary.

Method for Registering in Intraoral Measurements

Figure 7A:
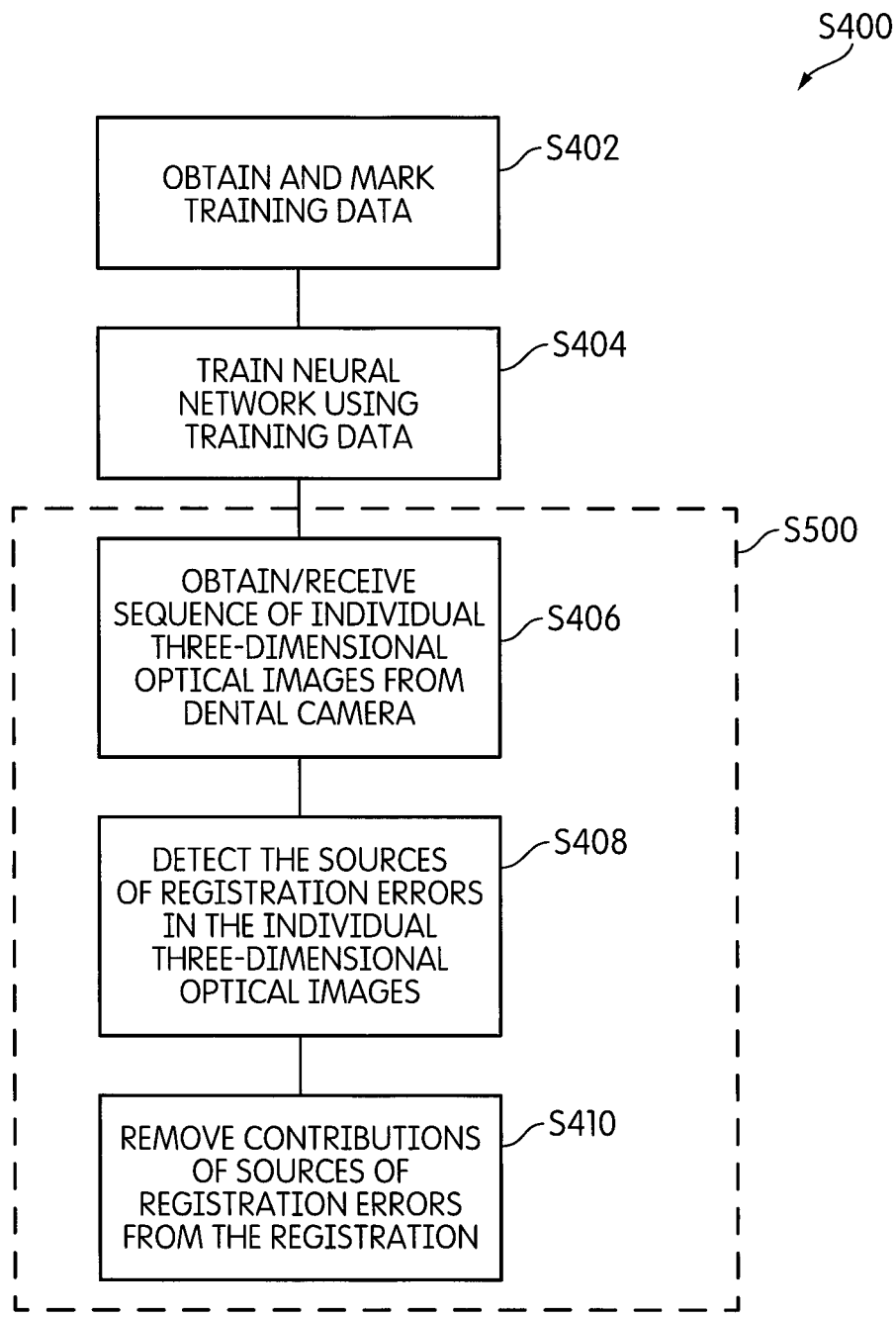
FIG. 7A is a flow chart illustrating a method according to an embodiment of the present invention.

Having described the system 200 of FIG. 3A reference will now be made to FIG. 7A, which shows a process S400 in accordance with at least some of the example embodiments herein.

The process S400 may begin by obtaining and marking areas of interest in the training data sets with predetermined labels, Step S402. For example, sample soft tissue 415 on sample image 413 shown in FIG. 3B (i) may be labelled as soft tissue. Sample hard tissue 412 on sample image 413 shown in FIG. 3B (i) may be labelled as hard tissue. The marking of the training images may be done digitally e.g. by setting dots on the images corresponding to the points of interest.

The training data may be labeled in order to assign semantics to the individual three-dimensional optical images 2. This may happen on a per-pixel level for color or depth information. Alternatively, meshes of complete 3D-models may be cut to compute corresponding per-pixel labels for single images. Moreover said meshes may be segmented such that the labeling process may be automated. These labels may distinguish between teeth, cheek, lip, tongue, gingiva, filling, ceramic while assigning no label to anything else. Irrelevant for the registration may be cheek, lip, tongue, glare and unlabeled data.

The training data may also be labeled in order to assign sources of registration error labels to the individual three-dimensional optical images 2. This may also be done on a per-pixel level, for example, for image or depth information. For example, the training data may be labeled on a pixel level for hard tissue 12 and for soft tissue 15 and/or instruments/intraoral applied disposables etc.

The semantic labels may overlap with markers for sources of registration errors, e.g. labels such as "Hard Tissue+ Glare", "Soft Tissue close to Hard Tissue", "Tongue+

HardTissue" etc. and these labels may be distinguishable from other labels such as "Cheek+Glare".

Using this set of labeled or classified images, a deep neural network 300 may be built and fed with the labeled images allowing the network to "learn" from it such that the network may produce a network wiring that may segment new images on its own.

As another option to segmentation involving classification on a on a per-pixel basis, segmentation may involve classification and training on a level slightly higher than a per-pixel level (i.e. on a per "super-pixel" level, i.e. "super-pixels" are parts of images that are larger than normal pixels of the image).

Instructions and algorithms of process S400 may be stored in a memory of the computer system 100 and may be loaded and executed by processor 122 to train (Step S404) one or more deep neural networks using the training data sets to detect one or more defects 15 based on one or more output labels/probability values. For example, if one of the probability values of the probability vector that corresponds to glare is 90%, then the neural network may detect glaring 21 as one of the sources of registration errors in the individual three-dimensional optical image 2.

The training may be done once, a plurality of times or intermittently. The training may also be semi- or self-supervised. For example, after a first training, the deep neural network may receive or obtain previously unseen images and the output, and corresponding feedback may be given such that the network may preferably operate on its own eventually to classify images without human help. Therefore, the deep neural network 300 may be trained such that when a sequence 8 of individual three-dimensional optical images 2 are input into the deep neural network 300, the deep neural network may return resulting labels/probability vectors for each image indicating the category in which parts of the images belongs.

After the training, the deep neural network may obtain or receive a sequence 8 of individual three-dimensional optical images from a dental camera 3 to segment in real time (Step S406) and may detect the sources of registration errors in the images (Step 408). Upon detecting said sources, the image registration module 206 may register the images together based on predetermined weights for the segments by ensuring that the detected sources of registration errors do not contribute to the registration process, Step S410. Steps S406-S410 of FIG. 7A are also included in the flow chart of FIG. 7B which is discussed hereinafter.

Figure 7B:
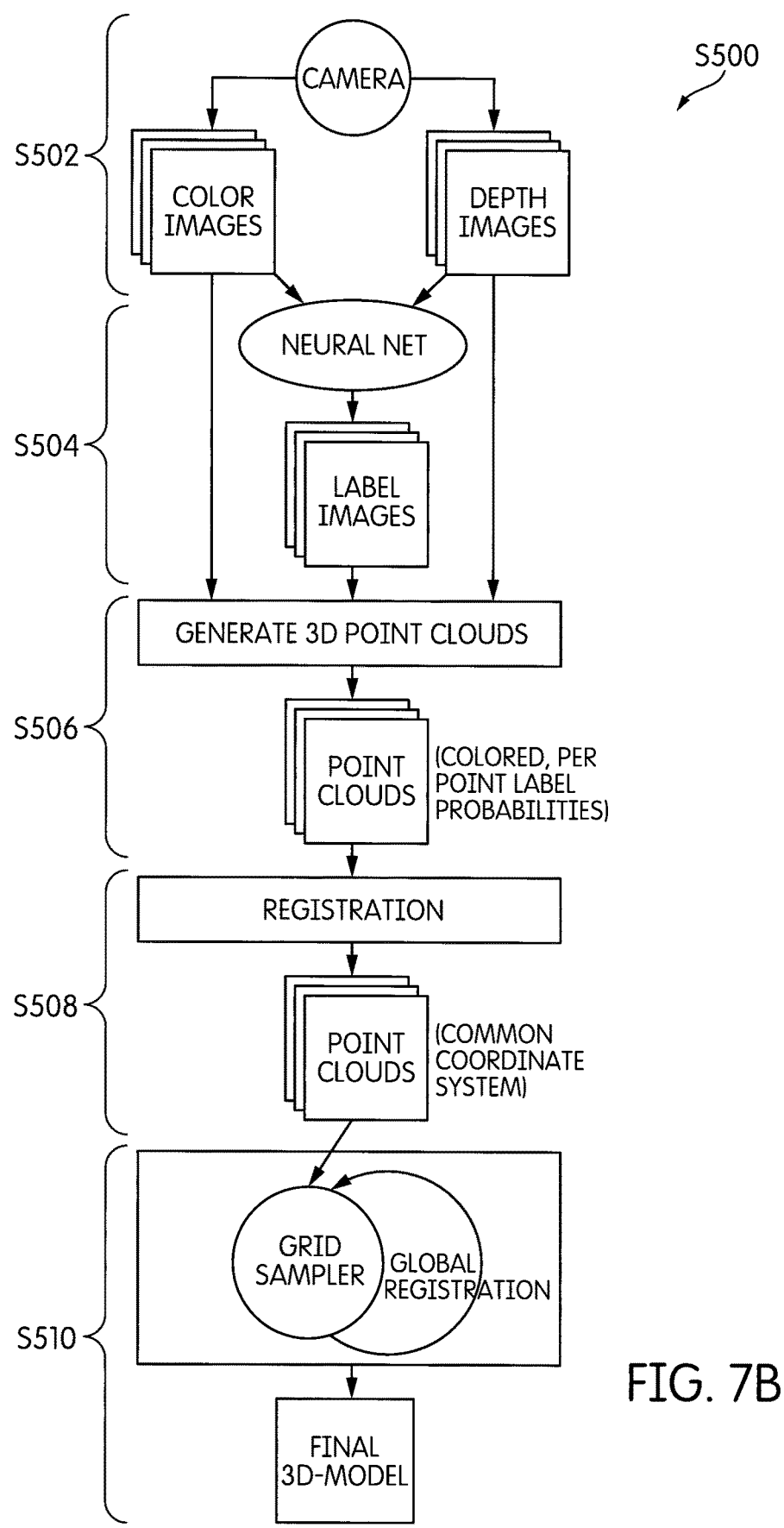
FIG. 7B is a flow chart illustrating a method according to an embodiment of the present invention.

FIG. 7B illustrates a process S500 which may be a subset of process S400. The process S500 may begin at Step S502 wherein color images and/or depth images are obtained from the dental camera 3. In Step S504, the color and depth images are used as inputs to the trained deep neural network 300 and corresponding output labelled images that show probabilities of the segments belonging to the object categories are obtained. Using both images may make it easier to discriminate between different labels. For example one would expected that it is harder to train a net to distinguish between soft and hard gingiva based on color than it is using depth and color. Since the images may be "mapped", which image is labeled may not make a huge difference. In an embodiment, one is labelled/segmented and the other may simply provide additional features to determine a segmentation. Depending on the embodiment, there may be a 1-to-1 correspondence between either resulting labelled image and depth image or resulting labelled image and color image. The labelled images may have the same lateral resolution as the depth/color images and a channel for the labels. In Step S506, a point cloud may be generated from the depth image by projecting each pixel of the depth image into space. To each point in the point cloud, a color value from the color image and a probability vector from the labelled image may be assigned. In an embodiment, labelled images, point clouds and resulting meshes may all have labels, label probabilities or probability vectors assigned to them. In Step S508, more images and corresponding output labels are obtained such that each incoming point cloud is registered to already registered point clouds. Herein, points with high probabilities (e.g. above a predetermined threshold or weighted as a function of the probability in a predetermined fashion) of being soft tissue are discarded or weighted less than other points with high probabilities of being hardtissue. In Step S510, each point in incoming point clouds is added to a corresponding grid cell to average position, color, and probabilities. Transformations that align single images to each other may then be optimized by the use of predetermined weights for soft tissue 15, hard tissue 12 and/or any other object categories. If a transformation changes, entries in the grid sampler may be updated accordingly. Of course, other embodiments different from FIG. 7B may be achieved in light of this description.

Computer System for Registering Intraoral Measurements

Figure 9:
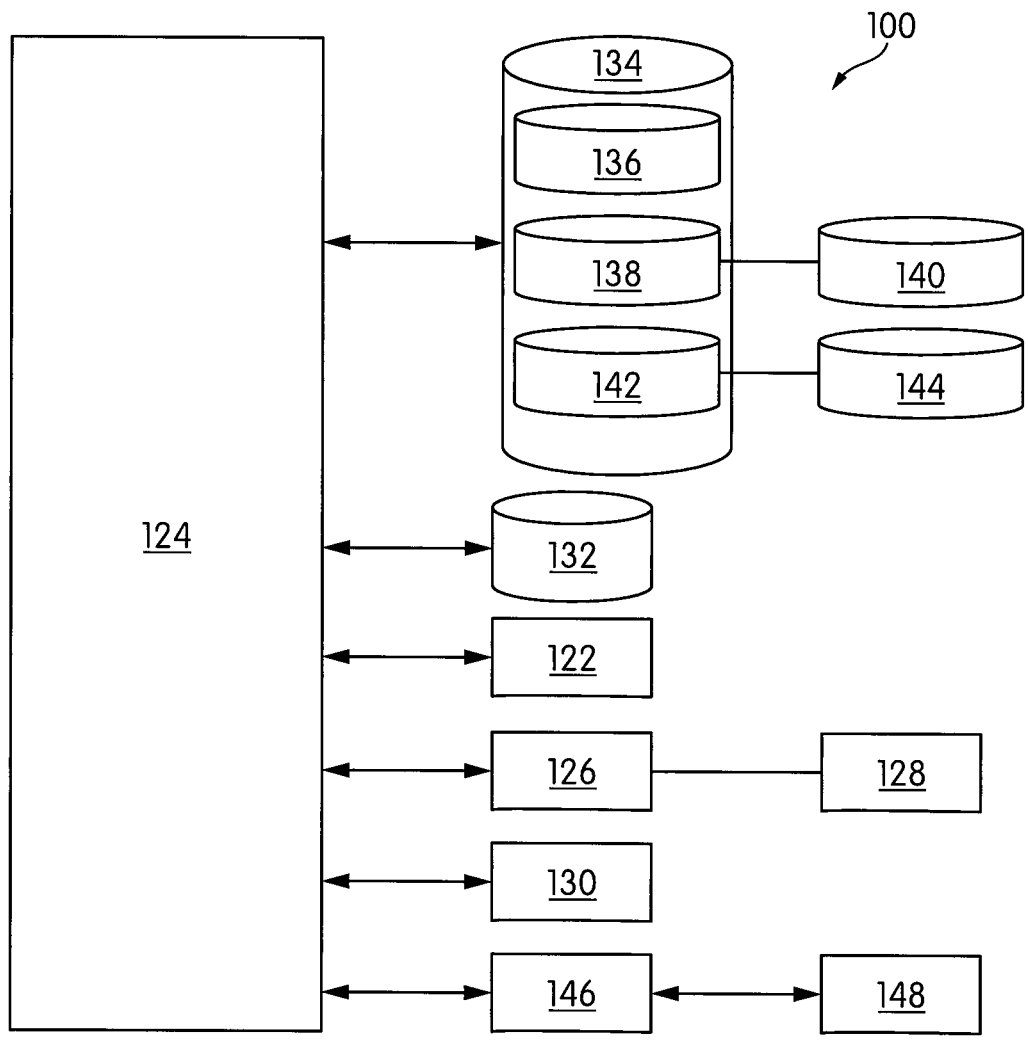
FIG. 9 is a block diagram showing a computer system according to an exemplary embodiment of the present invention.

Having described the processes of FIGS. 7A and 7B reference will now be made to FIG. 9, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the invention using other computer systems and/or architectures.

The computer system 100 may include or be separate from the training module 204, database 202 and/or image registration module 206. The modules may be implemented in hardware, firmware, and/or software. The computer system may also include at least one computer processor 122, user interface 126 and input unit 130. The input unit 130 in one exemplary embodiment may be used by the dentist along with a display unit 128 such as a monitor to send instructions or requests during the training process. In another exemplary embodiment herein, the input unit 130 is a finger or stylus to be used on a touchscreen interface (not shown). The input unit 130 may alternatively be a gesture/voice recognition device, a trackball, a mouse or other input device such as a keyboard or stylus. In one example, the display unit 128, the input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request for 3D measurement and may automatically detect sources of registration errors in the images, and automatically register the images based on the detected sources of registration errors using the image registration module 206. The processor 122 may achieve this by loading corresponding instructions stored in a non-transitory storage device in the form of computer-readable program instructions and executing the loaded instructions.

The computer system 100 may further comprise a main memory 132, which may be a random access memory ("RAM") and also may include a secondary memory 134.

The secondary memory 134 may include, for example, a hard disk drive 136 and/or a removable-storage drive 138. The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card, a wireless interface, ac loud delivering hosted services over the internet, etc.), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage.

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described herein.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for detecting scan interferences, to perform all or some of the methods described herein.

Implementation of other hardware and software arrangement so as to perform the functions described herein will be apparent to persons skilled in the relevant art(s) in view of this description.

What is claimed is:

1. A computer implemented method for three-dimensional (3D) registration, the method comprising:
    receiving, by one or more computing devices, individual images configured as depth and corresponding color images of a patient's dentition the depth and corresponding color images being mapped together;
    providing pixels of the individual images as input to a trained deep neural network;
    automatically identifying sources of registration errors in the individual images using one or more output label values of the trained deep neural network, wherein the output label values are obtained by segmenting the individual images into regions corresponding to one or more object categories;
    registering the individual images together based on the one or more output label values to form a registered 3D image that has no registration errors or substantially no registration errors,
    wherein the individual images are depth and corresponding color images that are mapped together by mapping the depth images to the corresponding color images or mapping the corresponding color images to the depth images
    wherein the method further comprises:
    generating a point cloud from the depth images by projecting pixels of the depth images into space:
    assigning, responsive to the generating, color values and label values to each point in the point cloud using the corresponding color images and the output label values of the trained deep neural network respectively; and
    based on the assigned label values, discarding or partially including one or more points in the point cloud using predetermined weights, such that the contributions of the discarded or partially included one or more points to registration is eliminated or reduced.

2. The method according to claim 1, wherein the individual images are individual three dimensional optical images.

3. The method according to claim 1, wherein the individual images are received as a temporal sequence of images.

4. The method according to claim 1, wherein the one or more object categories include hard gingiva, soft tissue gingiva, tongue, cheek, tooth and tooth-like objects.

5. The method according to claim 1, wherein an indication of a relevance of an identified source of registration error is based on its surrounding geometry.

6. The method according to claim 1, wherein the deep neural network is a network chosen from the group consisting of a Convolutional Neural Network (CNN), a Fully Convolutional Neural Network (FCN), a Recurrent Neural Network (RNN) and a Recurrent Convolutional Neural Network (Recurrent-CNN).

7. The method according to claim 1, further comprising:
    training the deep neural network using the one or more computing devices and a plurality of individual training images, to map one or more tissues in at least one portion of each training image to one or more label values,
    wherein the training is done on a pixel level by classifying the individual training images, pixels of the individual training images, or super pixels of the individual training images into one or more classes corresponding to semantic data types and/or error data types.

8. The method according to claim 7 wherein the training images include 3D meshes and registered pairs of depth and color images.

9. The method according to claim 8, wherein the 3D meshes are labelled and the labels are transferred to the registered pairs of 3D and color images using a transformation function.

10. A non-transitory computer-readable storage medium storing a program which, when executed by a computer system, causes the computer system to perform a procedure comprising:

receiving, by one or more computing devices, individual images configured as depth and corresponding color images of a patient's dentition, the depth and corresponding color images being mapped together;

providing pixels of the individual images as input to a trained deep neural network:

automatically identifying sources of registration errors in the individual images using one or more output label values of the trained deep neural network, wherein the output label values are obtained by segmenting the individual images into regions corresponding to one or more object categories:

wherein the individual images are depth and corresponding color images that are mapped together by mapping the depth images to the corresponding color images or mapping the corresponding color images to the depth images;

the procedure comprising registering the individual images together based the one or more output label values to form a registered 3D image having no registration errors or substantially no registration errors; and the procedure further comprising:

generating a point cloud from the depth images by projecting pixels of the depth images into space;

assigning, responsive to the generating, color values and label values to each point in the point cloud using the corresponding color images and the output label values of the trained deep neural network respectively; and based on the assigned label values, discarding or partially including one or more points in the point cloud using predetermined weights, such that the contributions of the discarded or partially included one or more points to registration is eliminated or reduced.

11. A system for three-dimensional (3D) registration, comprising a processor configured to:

receive, by one or more computing devices, individual images configured as depth and corresponding color images of a patient's dentition, the depth and corresponding color images being mapped together;

providing pixels of the individual images as input to a trained deep neural network;

automatically identify sources of registration errors in the individual images using one or more output label values of the trained deep neural network, wherein the output label values are obtained by segmenting the individual images into regions corresponding to one or more object categories:

wherein the individual images are depth and corresponding color images that are mapped together by mapping the depth images to the corresponding color images or mapping the corresponding color images to the depth images;

wherein the processor is configured to register the individual images together based the one or more output label values to form a registered 3D image having no registration errors or substantially no registration errors wherein the processor is further configured to:

generate a point cloud from the depth images by projecting pixels of the depth images into space;

assign, responsive to the generating, color values and label values to each point in the point cloud using the corresponding color images and the output label values of the trained deep neural network respectively; and based on the assigned label values, discard or partially include one or more points in the point cloud using predetermined weights, such that the contributions of the discarded or partially included one or more points to registration is eliminated or reduced.

12. The system according to claim 11, wherein the deep neural network is a network chosen from the group consisting of a Convolutional Neural Network (CNN), a Fully Convolutional Neural Network (FCN), a Recurrent Neural Network (RNN) and a Recurrent Convolutional Neural Networks (Recurrent-CNN).

* * * * *